United States Patent [19]

Aron nee Rosa et al.

[11] 4,309,998
[45] Jan. 12, 1982

[54] PROCESS AND APPARATUS FOR OPHTHALMIC SURGERY

[76] Inventors: Daniele S. Aron nee Rosa, 28 avenue Raphaël, Paris; Michele-Gabrielle R. Griesemann nee Laporte, 9 rue Alexandre Fleming, Bonneuil, Marne, Val-de-Marne, both of France

[21] Appl. No.: 46,630

[22] Filed: Jun. 8, 1979

[30] Foreign Application Priority Data

Jun. 8, 1978 [FR] France ................ 78 17111

[51] Int. Cl.³ .................................. A61N 5/00
[52] U.S. Cl. ........................ 128/303.1; 128/395; 331/94.5 M
[58] Field of Search ............ 128/303.1, 395–398; 331/94.5 M

[56] References Cited

U.S. PATENT DOCUMENTS

| | | | |
|---|---|---|---|
| 3,348,547 | 10/1967 | Kavenagh | 128/395 |
| 3,567,325 | 3/1971 | Tibbals, Jr. | 331/94.5 M |
| 3,703,176 | 11/1972 | Vassiliadis | 128/395 |
| 3,710,798 | 1/1973 | Bredemeier | 128/303.1 |
| 3,750,670 | 8/1973 | Palanos et al. | 128/303.1 |
| 3,821,510 | 6/1974 | Muncheryan | 128/303.1 X |
| 3,828,788 | 8/1974 | Krasnov et al. | 128/303.1 |
| 3,829,791 | 8/1974 | Schwartz | 331/94.5 M |
| 3,914,013 | 10/1975 | Rosenberg | 128/303.1 X |
| 3,947,688 | 3/1976 | Massey | 331/94.5 M |
| 3,971,382 | 7/1976 | Krasnov | 128/303.1 |

OTHER PUBLICATIONS

Liben et al., "An Argon Laser Photocoagulator", APL Technical Digest, vol. 11, No. 3, Jan.-Feb. 1972, pp. 2-14.

Primary Examiner—Lee S. Cohen
Attorney, Agent, or Firm—Armstrong, Nikaido, Marmelstein & Kubovcik

[57] ABSTRACT

Process and apparatus for ophthalmological surgery, wherein the apparatus includes a laser having a beam of power greater than $10^{12}$ Watts/cm$^2$ in one or more very short pulses of duration between 20 and 400 picoseconds. The laser beam is focussed by a strong conveying lens on tissue to be cut and has such low total energy that an optical puncture is produced without any notable thermal action. The apparatus employs a Q-switched YAG laser, with a helium-neon laser producing a registering or alignment beam. The laser beams are applied to a conventional slit lamp to enable them to be aligned at the target tissue, an electronic pulse selector may be included to select the exact number of pulses to be applied to the target.

12 Claims, 1 Drawing Figure

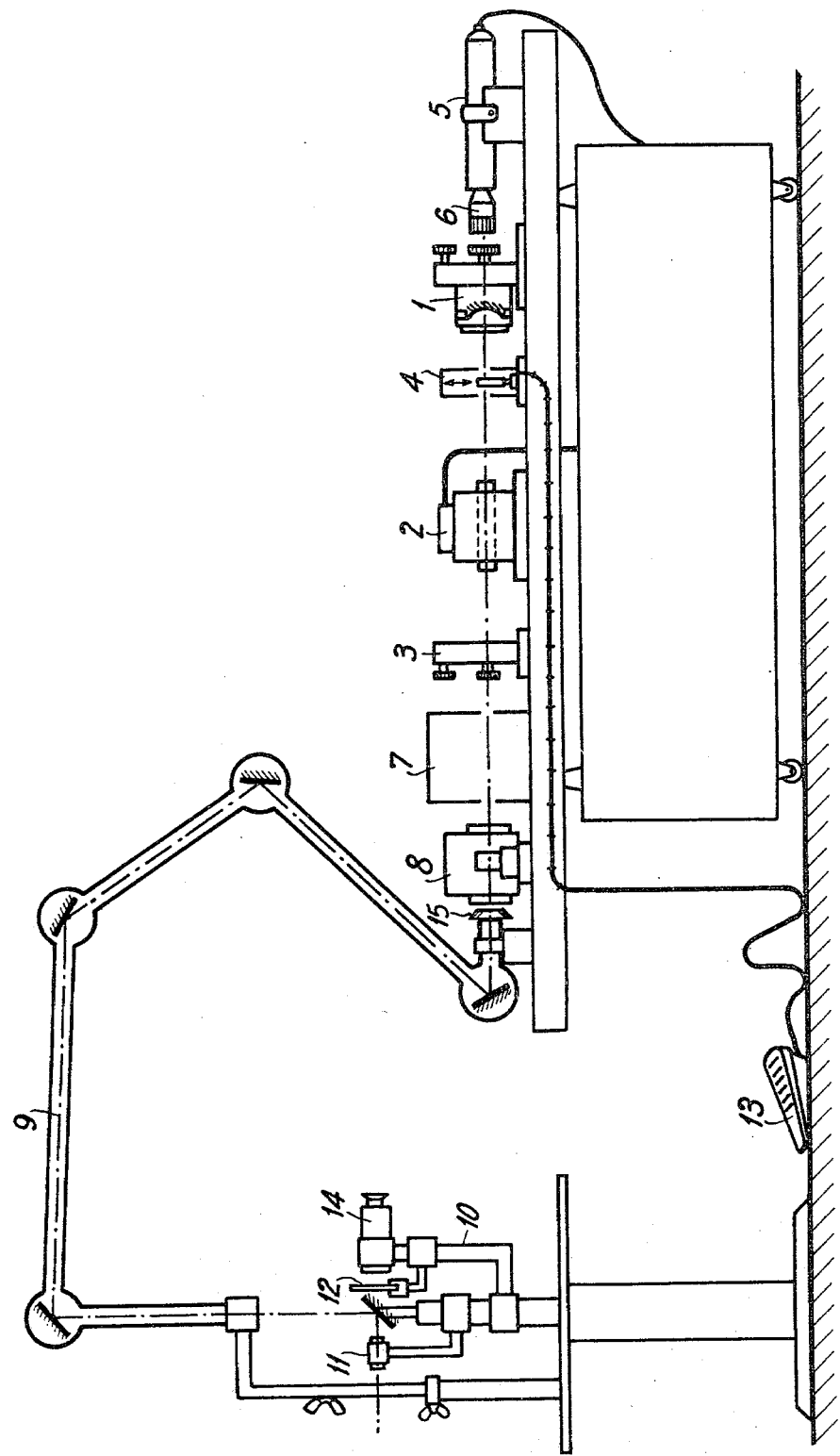

PROCESS AND APPARATUS FOR OPHTHALMIC SURGERY

The present invention relates to an apparatus for ophthalmological surgery, including at least one laser source, and a process for using the said apparatus, which is intended more especially, but not exclusively, for use in ophthalmological surgery.

PRIOR ART

It is known that laser sources are now currently used in various fields of surgery. Between 1965 and 1968 ruby lasers were used to try to operate on retinal coagulation.

These treatments were aimed at preventing the extension of a tear at the periphery of the retina or again to limit neo-vascular proliferations in the case of diabetic retinopathy. The lasers were used to produce light pulses having a wavelength of 6328 Å and a duration of several milliseconds and an energy of a few hundred milliwatts. In this operating method, the physical phenomenon consisted in transforming light energy into thermal energy in the layer of pigmented epithelium. However, in practice the method led to the frequent appearance of explosion bubbles and haemmorrhage bubbles in the vitreum and as a result the method has had very limited usage.

Photo-coagulators using argon lasers appeared after 1968. Their advantage lay in the excellent repeatability of their irradiation characteristics, their stability and the excellent absorption of the green radiation at 5140 Å produced by the laser in the pigmented epithelium and red vascularised tissues. These types of apparatus are always used with benefit and use powers ranging from 0.1 to 1.5 Watt carried by the pulses, of which the duration ranges from $10^{-2}$ to 1 second. The coagulation of pigmented protein substances results from a thermal action, the burn due to this action leading by the appearance of subsequent scar tissue to the formation of "spot welds on the retina". Unfortunately, radiation of this kind is ineffective on white tissue, unless powers that are harmful to the corneal endothelium are used. This same type of laser has sometimes been used to loosen, by burning the iridial sphincter, a compact myosis, using the pigmentation of iridial tissue to advantage.

Attempts to perforate the iris (iridotomy) have also been made using a continuous argon laser. Corneal lesions of thermal origin which have resulted from such treatment (of some glaucomas) have lead to its discontinuation. Iridotomy experimental operations using dye lasers, for example rhodamine 640, cresyl violet etc. emitting pulses of the order of 100 millijoules in 1 microsecond in the visible range have been carried out since 1978. Unfortunately, although the anatomical results have proved to be satisfactory, the traumatic nature of the treatment has resulted in a search for more pleasant methods of treatment for the patient.

Since 1974 there have been attempts to treat glaucomas with a ruby laser. The principle of this treatment is the re-opening of trabecula, which is tissue that, in its pathological state, ceases to be porous and obstructs the evacuation of aqueous humour through Schlemm's canal. Energies of the order of 200 millijoules carried by pulses of 50 nanoseconds have been focussed on trabecula surfaces of a diameter of 250 to 500 micrometers. The perforations obtained in this manner block up again within a period of at most two months by the appearance of scar tissue resulting from the thermal effects. In 1975, M. Krasnov published the results he obtained with a ruby laser or a neodymium laser in the treatment of soft cataracts and membranelles of secondary cataracts. As far as soft cataracts are concerned, the reabsorption of masses of the crystalline lens takes about one year after perforation of the anterior capsule of the crystalline lens by laser impact. In all these cases, a preliminary operation is necessary, the aim of which is to cause the coloured pigments of the iris to migrate to the white zones to be perforated. The presence of this coloured pigment is necessary for the effectiveness of lasers in this kind of treatment.

OBJECT OF THE INVENTION

An object of the present invention is to provide an apparatus enabling intraocular tissue to be cut without opening the eyeball, this cutting being independent of the chemical nature and the colour of the tissue. It seeks to achieve the cutting of tissue without heating the region undergoing cutting so that the operation does not give rise to relatively large areas of scar tissue.

Preferably, the apparatus allows adjacent tissue to be protected from the laser radiation.

In practice, the tissues to be cut using the present invention are:

the white masses of a crystalline lens affected by a cataract;

the transparent membranes of the crystalline capsule;

the transparent membranes or opacified membranes which result from a cataract operation (secondary cataract), the bands of condensation of vitreous humour that by their pulling cause or maintain tears in the retina.

On the other hand, the apparatus according to the invention must avoid any undesirable impact of the radiation on the cornea, the crystalline lens and the retina.

According to one aspect of the present invention there is provided a process for cutting biological tissue, especially in ophthalmic surgery, comprising the bombardment of tissue to be cut by a focussed laser beam, wherein the power density of the laser beam is greater than $10^{12}$ Watts/cm$^2$, the beam is pulsed, the duration of the or each pulse being between 20 and 400 picoseconds and the beam is passed through an optical system having a strong converging effect.

According to a second aspect of the present invention there is provided an apparatus for producing a directed and focussed laser beam suitable for cutting biological tissue, wherein the power density of the laser beam is greater than $10^{12}$ Watts/cm$^2$ in pulses of duration between 20 and 400 picoseconds and the beam is passed through an optical system having a strong converging effect, and the apparatus includes a laser oscillator including a bar of yttrium aluminium garnet doped with neodymium arranged to produce short trains of pulses.

In order that the invention may be fully understood and readily carried into effect it will now be described with reference to the single FIGURE of the accompanying drawing which shows in diagrammatic form one example of apparatus according to the invention.

THE PHYSICAL PROCESS

In the application of the invention, the high level of power density of light flux, greater than $10^{12}$ W/cm$^2$, is the determining factor in the physical process of interaction between the radiation and the material, and this process enables localised destruction of tissue without the occurrence of thermal action and without requiring the target to be pigmented. This process may be described in the following manner:

(a) Multiphotonic ionisation.

Although the ionisation potentials of atoms forming living matter (N, H, C, O) are all greater than 10 eV, and although the energy carried by a photon of which the wavelength λ, equal to 1.06 micrometers, is only 1.18 eV, the intensity of the light flux is strong enough to allow simultaneous action of a sufficient number of photons to effect in the material the transition from the electrically neutral state to the formation of a cloud of free electrons.

(b) Absorption of energy by electrons.

This concerns the transfer of kinetic energy from the electrical field of the light wave to liberated electrons. Through the process currently denoted by the expression "inverse bremsstrahlung", electrons from collisions with atoms and ions transform this directed kinetic energy into thermal electron energy and by a collision process in cascade transfer the ionisation state and the electron energy into the surrounding medium. At this stage a plasma that is opaque to radiation is created.

(c) Propagation of an electronic conduction wave.

In the first hundreds of picoseconds which follow the radiations and over a diameter of the order of 100 micrometers around the impact, it is the electronic conduction wave which is propagated, gradually yielding its energy to heavy particles, that is, the atoms and ions.

(d) In the several nanoseconds that follow, a hydrodynamic shock-wave is propagated through the tissue, but with an attenuation that is inversely proportional to the cube of the distance ($1/R^3$), and provides the mechanical action of cold destruction.

A process resulting from the use of the invention avoids the appearance of considerable scar tissue and it also avoids raising the temperature of transparent tissue traversed by the radiation, so that the tissue is not destroyed. The invention enables surgical cutting of tissue to be carried out by "optical puncture", by concentrating ultra-short light pulses from a laser by means of focussing lenses.

DESCRIPTION OF THE EMBODIMENT OF THE APPARATUS

Other features and advantages of the invention will become apparent from the following description of the particular embodiment shown in the single FIGURE of the accompanying drawing. Such apparatus for ophthalmological surgery is known as a Vitreotome or Vitrectome.

In the single FIGURE, the apparatus forming the subject of the invention includes a laser oscillator consisting of:

a cell 1 containing a mirror and a solution of a saturable absorbent, for example, KODAK 9740;

a laser 2 containing a rod of yttrium-aluminium-garnet (YAG) doped with neodymium;

a Fabry & Perot interferometer 3 which closes the resonant cavity and enables the duration of pulses to be selected from between 20 and 400 picoseconds;

an electrically controlled shutter 4, the "screen" of which is formed by a plate of Schott KG3 glass absorbing in the infrared region but allowing a visible marker beam from a low-power (1 milliwatt) helium-neon marker laser 5 to pass through, the marker laser having a beam of power 1 milliwatt and being arranged to coincide with the infrared beam of the operating laser 2. An afocal optical system 6 enables the divergence of this marker beam to be adjusted such that its focal point coincides with that of the operating laser 2 at the operation point.

There are also shown in the FIGURE, although their provision is optional and dependent on the therapeutic effects desired, an electro-optical device 7 allowing only one of the pulses of a train emitted by the laser 2 to be transmitted, and a potassium di-phosphate (KDP) crystal 8 converting the wavelength of the emission of 10645 Å from the laser 2 into green radiation of 5322.5 Å, with a view to carrying out a conventional photocoagulation operation.

The beam is carried as far as a slit lamp 10 such as is used in conventional ophthalmology through a hollow articulated arm 9, having mirrors at the joints to reflect this beam to the slit lamp 10. The slit lamp 10 is provided with an optical system including lenses 11 for focussing the laser beam so as to concentrate it at the operating point.

A pedal control 13 controls the opening of the shutter 4 leaving the hands of the operator free to adjust the alignment of the marker beam with the operation site. When the shutter is open, the YAG laser 2 which is released at a rate of from 1 to 0.3 Hz emits a train of pulses which is used for the surgery; an electrical circuit, such as a monostable, (not shown) prevents the emission of a second train of pulses by automatically closing the shutter 4 after a certain time. A further press on the pedal 13 is necessary to obtain another train of pulses.

The slit lamp 10 is provided with a plate 12 of Schott KG3 glass, positioned on the optical axis of the viewing eyepiece 14 which enables the marker beam to be observed whilst protecting the eyes of the operator against the possible reflections of the operating beam.

Using a bar 2 of yttrium-aluminium-garnet doped with neodymium as the active component, the laser oscillator emits pulses of infrared light at a wavelength of 10645 Å, as mentioned above. These pulses are in the form of a burst, or a train of from 9 to 5 "spikes", each of a duration ranging from 20 to 30 picoseconds and separated by 6 nanoseconds. The energy contained in this train of "spikes" when it leaves the laser oscillator ranges from 10 to 15 millijoules. This type of emission is ensured by the operation in a system of mode locking of the laser oscillator and is due to the presence in the cavity of the cell 1 containing Kodak 9740 saturable absorbent. The cell 1 continuously circulates the absorbent in front of one of the mirrors of the cell (thickness of the absorbent traversed = 1 millimeter).

It may be useful to use only a single pulse for a bombardment. In this case, the selection may be effected by a pulse selector 7 of the type manufactured by the Société Quantel or the British company, J. K. Lasers.

The light beam emitted by the laser oscillator 1, 2, 3, 4 may be passed into an optical system consisting of lenses 15, intended to increase the diameter of the beam so that the average light flux in a cross-sectional plane of the said beam is less than a threshold value that causes damage to conventional metallic mirrors so that these can be used instead of the multidielectric mirrors which would be required by a more concentrated beam. Typically, the optical system multiplies the diameter of the said beam by a factor 20.

The light beam is then conveyed by a series of mirrors contained in the hollow articulated arm 9 to the slit lamp 10. The first mirror of the series in the arm 9 is a dielectric mirror reflecting the infrared light from the YAG laser but transparent (i.e. only partially reflective) to the light of the helium-neon laser 5 which, being aligned with the beam from the YAG laser, allows the point of impact on the target to be observed and visibly adjusted.

An optical arrangement may be mounted on the helium-neon laser 5, to enable the divergence of the red beam from the laser 5 to be modified so that, at the point of impact, the red focal point coincides with that of the infrared light from the YAG laser.

At the light beam inlet at the top of the slit lamp 10, a container holds another dielectric mirror able to reflect infrared light but transparent to visible light; this particular mirror permits (a) the passage into the axis of the slit lamp of white light permitting the operating field to be treated to be illuminated for examination by the operator;

(b) the power of the red marker beam to be limited to a value below the threshold of danger defined by international standards (reflection in red: 4%);

(c) the infrared energy necessary for treatment to be preserved unattenuated.

The red and infrared laser beams are focussed by a pair of achromatic converging lenses 11 of a power of 10 diopters positioned on the axis of the slit lamp 10 and at a distance such that, taking into account the final reflection, by a mirror, into a horizontal direction, the focussing point is situated precisely in the plane of clear sight of the biomicroscope of the lamp 10.

The protection of the operator against the reflections of laser light is provided by the presence in the biomicroscope of the fixed filter 12 consisting of a plate of Schott KG3 glass of 5 mm thickness, which is transparent in the visible region and attenuates by a factor $10^8$ in the infrared region.

The infrared light energy contained in the trains of pulses used in the operations described below varied from a minimum of 2 millijoules and a maximum of 5 millijoules.

The dimensions of the focal spots are adjustable using the optical lens devices from 50 to 100 micrometers in diameter.

The combination of the minuteness of the focal spots, the extreme brevity of the light spikes, the modest nature of the energies brought into play and the strong convergence of a beam of large diameter (15 mm) is the determining factor which has enabled the zone of tissue to be destroyed to be defined very precisely and has enabled thermal effects to be eliminated.

The high power densities thus used ($10^{12}$ Watts/cm$^2$) have proved to be a safety factor for the retina located beyond the focal point; in fact, they ensure that the target, even when it is transparent, is turned into a gas of electrons and ions, a plasma of which the electronic density is greater than the critical density for which this gas becomes opaque to radiation (for a wavelength of 10645 Å, this critical density is $10^{21}$ electrons/cm$^3$). The "optical puncture" effected by the light pulse therefore provides its own screen.

The strong convergence of the beam itself is also a safety factor for the following reasons:

(a) the strong postfocal divergence ensures scattering of the small proportion of light transmitted beyond the focal point so that the resulting intensity of this radiation falling on the retina is harmless;

(b) this strong convergence ensures that before the focal point is reached there is sufficient spread of the beam to render it harmless to the transparent surfaces located in front of the point to be destroyed and traversed by the beam.

It will be noted that the corneocrystalline lens system is included as a converging element in the path of the beam, such that the beam is never able to converge on the retina, the furthest point of focussing being more than 3 millimeters away from the retina.

The apparatus also advantageously includes a further glass cell having parallel faces and containing a solution of Kodak 9740 saturable absorbent. The cell is located in the path of the beam downstream of the Fabry & Pérot interferometer. This glass cell, sited outside the cavity or cell of the laser oscillator, must be out of alignment with respect to the beam itself. The purpose of this cell is to render difficult or impossible the operation of the laser between the target and the windows of the cell 1. The absence of this cell means that it would be possible for the laser to work in free-running operation between the windows of the cell 1 and the target on which the beam is focussed. Under these conditions, the laser operates in a millisecond mode and is not effective. The presence of this cell is essential for the good "mode locking" of the laser.

The slit lamp 10 is a standard ophthalmic instrument and the lasers and other components are obtainable from the Société Quantel.

EXAMPLES OF USE OF THE APPARATUS

The experimental treatments carried out on human patients involved four types of cases.

(1) Congenital cataracts

Of six cases of congenital cataract, with the age of the patients ranging from 8 to 13 years, and the crystalline lenses being perfectly white, five were soft cataracts and one was a not very thick but hard cataract.

In the case of the hard cataract, it was possible in two sessions of 250 to 300 impacts (about 7 minutes) to liberate the visual axis, restoring to the patient an acuity of the order of 1/10 distant vision and $P_8$ close vision on the Parinaud scale, a result that was predictable after 12 years of amblyopia but nevertheless very satisfying.

In the other cases, despite the complete absence of coloured pigment, it was possible to open the anterior crystalline lens capsule by adjoining perforating impacts.

The masses were reabsorbed spontaneously in a week, largely re-opening the visual axis and restoring an acuity ranging from 3 to 7/10° distant vision.

No lesion of the hyaloid appeared neither was there any anaphylactic or inflammatory reaction.

(2) Traumatic cataracts

Two cases of traumatic cataracts were treated, these being cataracts completely devoid of coloured pigment.

Five to six sessions of 200 to 250 impacts spaced out over a week enabled the visual axis to be freed with a resultant acuity of vision of from 6 to 9/10° with correction.

All the above-mentioned cases had a reduced acuity to perception of light before treatment.

(3) Secondary cataracts or cataracts of membranelles

Nineteen cases of secondary cataracts were treated. These membranelles result from opacification of the posterior capsule of the crystalline lens after extracapsular operation on the cataract.

Thirteen cases involved opaque white membranelles, having no pigment, which it was possible to open in one to three sessions of 250 to 300 impacts.

Five cases involved stretched translucent membranelles which limited visual acuity to 1/10° at best. In these cases, a session of 5 to 450 impacts was still sufficient to restore to the patient a visual acuity from 8/10° to 12/10° with suitable correction.

Opening by adjacent impacts along two perpendicular axes seems the easiest as the traction exerted contributes to the liberation of the axis.

The last case was that of a secondary cataract membranelle located behind an artificial crystalline lens (intra-ocular implant). In this case, it was possible to make the circular opening in the membranelle through the implant. Marks occurring accidentally on this implant from uncontrolled movements of the eyeball did not in any manner hinder the good visual acuity obtained (7/10°).

(4) Access to the vitreum

Intracapsular intervention in the cataract requires subsequent opening of the transparent vitreous hyaloid.

In four cases treated, four openings of this transparent membrane were effected with success.

The vitreous bands are bands or strips of coagulated vitreous humour. They are translucent or white and their existence involves, through the traction that they exert, a risk of detaching the retina, where they become attached to it. They may also, in certain cases, hold lifted up the flaps of a tear in the retina.

In six cases treated, it was possible in each case to cut these bands or strips either directly or through a three-mirror lens of the Goldman type. Again, and in all the cases, cutting was effected by adjacent perforating impacts.

In the existing state of this apparatus, the temporary characteristics of the irradiation (bursts of several extremely short pulses) had the effect of rebounding the destroying action towards the operator over a distance of about 2 mm. It is therefore necessary for the present to maintain a safety distance of 3 mm between the target and any surface positioned up stream of it that is not to be harmed.

It will be apparant that modifications may be made to the embodiments that have just been described, especially by substituting equivalent technical features, without departing from the present invention for example, other types of laser than those specified may be used.

We claim:

1. A process for cutting biological tissue including transparent tissue in ophthalmic surgery, comprising bombarding tissue to be cut with a focussed pulsed laser beam, wherein the power density of the laser beam is greater than $10^{12}$ Watts/cm$^2$, and the duration of each pulse being between 20 and 400 picoseconds, the pulses being in the form of a train of from 5 to 9 spikes having a total energy of from 2 to 5 millijoules, the beam being passed through an optical focussing system having a strong converging effect.

2. A process according to claim 1 wherein the wavelength of the laser beam is 10,645 Å, said wavelength being selected to remain in the range for which the cornea is transparent.

3. A process according to claim 2 wherein the optical focussing system has a power of the order of 10 diopters.

4. Apparatus for producing a directed and focussed laser beam suitable for cutting biological tissue including transparent tissue in optical surgery, comprising a laser oscillator producing a pulsed beam, the power density of which is greater than $10^{12}$ Watts/cm$^2$ and an optical focussing system having a strong converging effect aligned in the path of the beam of the laser oscillator between the oscillator and the tissue to be cut, and the laser oscillator including a rod of yttrium aluminum garnet (YAG) doped with neodymium emitting short trains of light pulses at a wavelength of 10645 Å.

5. Apparatus according to claim 4 including a solution of Kodak 9740 saturable absorbent in a cavity in the laser oscillator for effecting mode locking of the laser oscillator.

6. Apparatus according to any of claims 4 or 7 further including optical means downstream of the laser oscillator for enlarging the diameter of the laser beam to reduce the intensity of the beam.

7. Apparatus according to any of claims 4 or 5 further including an external KDP crystal cell downstream of the laser oscillator through which the laser beam can pass to effect a wavelength conversion on the beam radiation.

8. Apparatus according to any one of claims 4 or 5, including a pulse selector in the path of the beam of the laser oscillator adapted so that only one pulse from a train of pulses is allowed to pass through.

9. Apparatus according to any one of claims 4 or 5, including a glass cell having parallel faces and containing a solution of Kodak 9740 saturable absorbent arranged in the path of the beam outside the cavity of the laser oscillator.

10. Apparatus for ophthalmic surgery according to any one of claims 4 or 5, further comprising a Fabry and Perot interferometer aligned with the path of the beam of the laser oscillator, and a wavelength converter for changing the wavelength of a beam from the laser oscillator aligned with the path of the beam of the laser oscillator downstream of said interferometer.

11. Apparatus according to any of claims 4 or 5 further including an auxiliary laser source emitting a marker beam of visible radiation aligned with the beam of the laser oscillator, an optical arrangement at the exit of the auxiliary laser source to enable the divergence of the visible beam to be modified so that the visible focal point coincides with that of the infrared focal point of the YAG laser oscillator, and a plate of glass aligned in the beam of the laser oscillator absorbing the wavelength of the YAG laser but allowing the visible radiation from the auxiliary laser to pass through, arranged in a shutter operatively associated with the laser oscillator for effecting on/off-switching.

12. Apparatus according to claim 11 including a plate of Schott KG3 glass positioned on the optical axis of a viewing eyepiece aligned with the path of the laser beam to the tissue to be cut which enables the marker beam to be observed whilst protecting the eyes of an operator against the possible reflections of the YAG laser oscillator beam.

* * * * *